United States Patent
Sens et al.

(10) Patent No.: US 7,847,930 B2
(45) Date of Patent: Dec. 7, 2010

(54) HIGH-SENSITIVITY METHOD FOR DETECTING DIFFERENCES BETWEEN THE PHYSICALLY MEASURABLE PROPERTIES OF A SAMPLE AND A REFERENCE

(75) Inventors: Ruediger Sens, Ludwigshafen (DE); Erwin Thiel, Wilnsdorf (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 468 days.

(21) Appl. No.: 11/722,757

(22) PCT Filed: Dec. 21, 2005

(86) PCT No.: PCT/EP2005/013775
§ 371 (c)(1),
(2), (4) Date: Apr. 16, 2008

(87) PCT Pub. No.: WO2006/069695
PCT Pub. Date: Jul. 6, 2006

(65) Prior Publication Data
US 2008/0304059 A1    Dec. 11, 2008

(30) Foreign Application Priority Data
Dec. 23, 2004  (DE) .................. 10 2004 062 256

(51) Int. Cl.
*G01J 1/10* (2006.01)
(52) U.S. Cl. ................................... 356/243.5
(58) Field of Classification Search .................. None
See application file for complete search history.

(56) References Cited

U.S. PATENT DOCUMENTS 7,242,477 B2 *   7/2007   Mieher et al. ............... 356/401
7,289,213 B2 *  10/2007   Mieher et al. ............... 356/401

FOREIGN PATENT DOCUMENTS

| EP | 0 908 716 | 4/1999 |
| GB | 1 315 318 | 5/1973 |
| WO | 2005 019808 | 3/2005 |

* cited by examiner

*Primary Examiner*—Tu T Nguyen
(74) *Attorney, Agent, or Firm*—Oblon, Spivak, McClelland, Maier & Neustadt, L.L.P.

(57) ABSTRACT

A method for detecting differences between physically measurable properties of a sample and a reference sample. A two-dimensional reference field is generated and first and second two-dimensional patterns are produced respectively from the reference sample and the sample. A correction is made to sample response functions to eliminate time-dependent and location-dependent fluctuations of the detector.

18 Claims, 4 Drawing Sheets

HIGH-SENSITIVITY METHOD FOR DETECTING DIFFERENCES BETWEEN THE PHYSICALLY MEASURABLE PROPERTIES OF A SAMPLE AND A REFERENCE

BACKGROUND

1. Field

The invention relates to a highly sensitive method for the detection of differences between the physically measurable properties of a sample and a reference.

The invention relates in particular to a method for the detection of the change in a physically measurable property of a sample brought about by an environmental influence.

2. Description of Related Art

For the industrial production of dyes, pigments, coatings, UV stabilizers and sun protection agents, it is of critical importance to know the light fastness of the products. At the present time, the light fastness of a product is measured by the product being irradiated with light of which the spectral distribution corresponds to that of sunlight on the surface of the earth. Following irradiation, the color change is quantified with the aid of reference systems. The disadvantage with this procedure is the to some extent very long irradiation times which are necessary in order to make a color change detectable in many products. For example, according to the relevant DIN Standards, the irradiation times are 1000 hours and more. For very light-fast samples, they are 10 to 50 years. A reference is then made against a color scale, for example the blue wool scale. The disadvantage with this procedure is, furthermore, that a human being has to make the assessment and this assessment is therefore determined by a subjective impression.

Examples of samples which need particularly long exposure times are façade paint, express highway signs, sealing materials for buildings, electrical insulators, roof tiles and safety panels. Further samples are mentioned in the standards below for exposure and weathering.

Relevant standards for weathering with artificial daylight are ISO 4892 (1994) for plastics, ISO 11341 (1994) for coatings and paints, ISO 11507 (1997) for coatings in instruments, ISO 3917 (1999) for road vehicle safety panels, ISO 11431 (2002) for civil engineering joint sealing materials, ISO 105-B02 (1994) for textile color fastness checks and ISO 105-B04 (1994) for textile color fastness weathering.

Relevant standards for direct weathering are ASTM G7, ISO 877, ISO 2810, ASTM D4141C (Black Box) and ASTM G24 (exposure under glass).

SUMMARY

With the object of reducing the necessary radiation time, the products are frequently irradiated with a multiple of the intensity of the sun. However, it has been shown that the light fastnesses measured with increased irradiation intensity frequently do not agree with those which are present under natural conditions. In other words, the color change $\Delta F$ produced in the irradiated sample depends not only on the product of intensity I and irradiation time $\Delta t$, designated the radiation dose S, but also explicitly on the intensity I of the radiation $\Delta F = f(S, I)$.

It is an object of the invention to provide a measuring method with which the color change on a sample induced by light can already be determined after a short irradiation time without irradiation conditions differing from natural conditions having to be used.

The object is achieved by a method for the detection of differences between the physically measurable properties of a sample P and of a reference sample R, in which (i) a sample P is provided,
(ii) a reference sample R is provided,
(iii) a two-dimensional reference field RF is provided,
(iv) a first two-dimensional pattern is produced from regions of the reference sample R and from the reference field RF, and a second two-dimensional pattern is produced from regions of the sample P and of the reference field RF, the first and second patterns being described by a location-dependent and wavelength-dependent pattern function $M(x, y, \lambda)$,
(v) for the first pattern, at a freely selectable time $t_0$ and for the second pattern, at the time t, by means of a detector, the transmission, reflection or scattering of analytical radiation by the first pattern and the second pattern, respectively, is detected as a function of the local coordinates (x, y) of the first and second pattern and of the wavelength $\lambda$ of the analytical radiation and thus
    a first pattern response function $M_0(x, y, \lambda, t_0)$, which contains physically separated regions of a reference response function $R_0(x, y, \lambda, t_0)$ and of a first reference field response function $RF_0(x, y, \lambda, t_0)$, is determined for the first pattern,
    a second pattern response function $M_t(x, y, \lambda, t)$, which contains physically separated regions of a sample response function $P_t(x, y, \lambda, t)$ and of a second reference field response function $RF_t(x, y, \lambda, t)$, is determined for the second pattern,
    the functions $M_0$ and $M_t$ in each case reproducing the intensity of the transmitted, reflected or scattered analytical radiation as a function of the local coordinates (x, y) of the first and second pattern, respectively, and of the wavelength $\lambda$ at the different times of the detection to and t,
(vi) a correction to the sample response function $P_t$ is made in such a way that, by means of the first and the second reference field response function $RF_0$ and $RF_t$, the detector-induced location-dependent and time-dependent fluctuations are eliminated from the sample response function $P_t$, a corrected sample response function $P_{t,corr}$ being obtained,
(vii) the change in the physically measurable property is determined from the corrected sample response function $P_{t,corr}$ and the reference response function $R_0$.

BRIEF DESCRIPTION OF THE DRAWINGS

The disclosure will be better understood from reading the description which follows and from examining the accompanying figures. These are provided solely as non-limiting examples of embodiments. In the drawings.

DETAILED DESCRIPTION

According to the invention, a correction is made to the sample response function from the sample in order to eliminate the time-dependent and location-dependent fluctuations of the detector, for example a scanner, which are present. This method step will also be designated the reference field correction in the following text. For this purpose, in step (v), the transmission, reflection and scattering of the analytical radiation are additionally detected by means of a reference field which surrounds or penetrates the sample or reference sample, and in this way a reference field response function is determined. For the reference field, it is assumed that it is spatially homogeneous and constant over time. From the location-dependent, time-dependent and wavelength-dependent fluctuations of the reference field response function, in this way the location-dependent, time-dependent and wavelength-dependent fluctuations of the detector are determined and the response function is corrected appropriately. Thus, from the sample response function $P_t$ determined at the time t, by means of local, temporal and spectral correction by using the reference field response functions at the time $t_0$ and t, respectively, a corrected sample response function $P_{t,corr}$ is obtained.

The reference field can surround or penetrate the sample or reference sample. For example, the sample can be arranged as a small rectangle within a larger rectangular reference field. The reference field can penetrate the sample as a bar code pattern or checkerboard pattern. The bar code or checkerboard pattern can additionally be arranged as a small rectangle within a larger rectangular reference field. Any further desired arrangements are conceivable. The arrangement of reference field and sample or reference sample is described by a location-dependent and wavelength-dependent pattern function $M(x, y, \lambda)$. The response functions for reference sample and reference field and sample and reference field respectively, are contained in the measured first and second pattern response functions respectively. These measured pattern response functions are used to carry out a correction to the sample response function with the aid of suitable mathematical operations, and in this way to eliminate the location-dependent, time-dependent and wavelength-dependent detector fluctuations.

The reference sample is preferably an untreated sample, of which the response function $R_0$ is determined at the time $t_0$. The sample is a treated sample, of which the response function $P_t$ is determined at the time t. If a plurality of response functions are determined for the treated sample at a plurality of different times $t_i$, then a plurality of (time-dependent) response functions $P_{ti}$ are obtained and the abovedescribed correction is carried out for each time $t_i$.

In a first step (i), a sample P is provided. The sample P can differ from the reference sample R, these differences being manifested in the physically measurable properties of the sample P and reference sample R. The purpose of the method according to the invention is to detect the existence or absence of these differences and/or to register these differences quantitatively. For example, with the method according to the invention, the fastness to weathering of a paint sample can be determined.

The provision of the sample P in the first step (i) preferably comprises the treatment of a sample, the treatment consisting in the sample being subjected to an environmental influence. The sample is in particular a substrate surface. Here, the substrate surface to be examined is subjected to an environmental influence. Environmental influences in the sense of the present invention are any desired external actions on the sample which are suitable to change its physically measurable properties. Environmental influences in the sense of the present invention comprise the action of light or—more generally—radiation, of mechanical forces, of chemicals, of gases, of microorganisms, of radioactive radiation, of sound (for example ultrasound) and of heat on the substrate surface. The environmental influence can be effected, for example, by irradiation or weathering of the substrate surface or by applying chemicals onto the substrate surface. Here, "chemicals" means all substances or mixtures of substances (for example including cosmetic formulations) which can react with the substrate surface or with the substances contained in the latter. The environmental influence can also include an interplay of a plurality of the external influences mentioned by way of example above. For example, in the case of photooxidation, light and atmospheric oxygen interact. In the case of weathering trials in the open air, the weathered samples are generally subjected to the action of light, chemicals (water, acids, etc.), gases, microorganisms, heat and mechanical actions (wind, rain).

The properties of the substrate surface are physically measurable in the sense of the present invention if they can be registered by the interaction of the sample with an analytical radiation radiated onto the sample or into the sample. Analytical radiation can be any desired radiation which is able to interact with the sample and to be transmitted, reflected or scattered by it. Examples are electromagnetic radiation, particulate radiation (neutrons, and radioactive alpha or beta radiation) or acoustic radiation (for example ultrasound)

The term 'the sample' covers an extremely wide range and comprises in general objects which can specifically be subjected to specific environmental influences. For example, the sample can be a substrate coated with a pigment layer, which is subjected to UV radiation in order to examine the light fastness of the pigment layer. The sample can be a field which, in order to examine the effectiveness of herbicides or fungicides, is treated with these and subsequently photographed from the air. If the abrasion resistance or weathering resistance of façade coatings is to be examined, then the sample can be a wall of a building, which is weathered naturally or subjected to a sand blast.

It is possible for only changes in the properties close to the surface to be induced by the environmental influence and subsequently detected. However, changes in the properties can also be induced in the interior of a sample by an environmental influence and subsequently detected. The latter also depends on the permeability of the sample to the environmental influence and the analytical radiation used. For instance, radiation can be reflected or scattered at the surface or else penetrate completely through the sample. Radiation can also be focused on to a plane in the interior of the sample by means of suitable apparatus and therefore the change in the property in this plane can be detected.

In one embodiment of the method according to the invention, the surface of a sample is examined. In the following text, the term "substrate surface" will also be used for the surface of a sample that is to be examined. In this case, the term covers not only the geometrically understood surface of the sample but also deeper layers of the sample lying underneath this geometric surface which are still accessible to the measurement by means of the selected physical method.

The environmental influence generally acts on the sample or substrate surface with a physically constant intensity. If the acting environmental influence is light with a specific wavelength or with a specific spectral distribution, then the intensity can be equated with the radiation intensity, which is measured in $W/cm^2$. If the acting environmental influence is the action of mechanical forces which, for example, are caused by a substrate surface being subjected to a sand blast, then the intensity of this environmental influence can be equated with the number of sand particles striking the substrate surface per unit time and unit area. If the acting environmental influence is the action of chemicals or gases, then the intensity of this environmental influence can be equated with the concentration of a specific substance at the location of the substrate surface. If the acting environmental influence is the action of microorganisms, then the intensity of this environmental influence can be equated with the number of microorganisms per unit area.

The sample is subjected to the environmental influence during a specific action period $\Delta t$. The action period $\Delta t$ depends on the type and intensity of the environmental influence and can be seconds, minutes, hours or days, for example one second to 10 days.

In a second step (ii), a reference sample is provided. The reference sample can be any desired sample of which the identity or non-identity with the sample is to be established. If a change in properties induced via environmental influences is to be established, the reference sample is an untreated sample. This has the same condition, at least at its surface, as the sample which is subjected to the environmental influence, that is to say, before the sample is subjected to the environmental influence, the sample and the reference sample are substantially identical with respect to their surface properties. The reference sample is not subjected to the environmental influence.

The reference sample can also be the sample itself before this is subjected to the environmental influence, that is to say the reference sample can be the untreated sample. The reference sample preferably is the untreated sample. This ensures that (untreated) sample and reference sample actually have identical properties.

In a third step (iii), a reference field is provided. The surface of the reference field preferably has the same properties as the reference sample.

In a fourth step (iv), a first two-dimensional pattern is produced from regions of the reference sample R and from the reference field RF, and a second two-dimensional pattern is produced from regions of the sample P and of the reference field RF, the first and second patterns being described by a location-dependent and wavelength-dependent pattern function $M(x, y, \lambda)$. The pattern function M can have but does not have to have an explicit wavelength dependence.

Of course, the performance of the steps (i)-(iv) is not bound to a specific order. Any practical order is possible.

The reference field can be, for example, a mask or stencil which has cutouts. The cutouts can have any desired geometric shapes and can be arranged as desired. The cutouts preferably have geometrically regular cutouts and are preferably arranged regularly. Examples are a checkerboard pattern or a bar code pattern. The pattern having regions comprising reference field and sample or reference sample is then produced by regions of the (reference) sample being arranged behind the cutouts or in the cutouts of the mask. For example, the (reference) sample can be placed behind the mask of the reference field, regions of the (reference) sample placed behind being visible through the cutouts of the mask. The (reference) sample can also be inserted into the cutouts or have elevations which are complementary to the cutouts of the mask and thus fit into the cutouts in the latter, the height of the elevations preferably corresponding to the thickness of the mask, which means that mask and (reference) sample can be connected to each other with a form fit and a pattern with a smooth surface is obtained.

Of course, the (reference) sample can also be formed as a mask with cutouts, and regions of the reference field can be arranged in the cutouts.

The stencil or mask is preferably a bar code mask, that is to say a mask having rectangular, regularly arranged cutouts.

Reference field, reference sample, sample and pattern can also be produced as follows: the untreated surface of a sample to be examined is partly covered with a mask which has cutouts and is then subjected to the environmental influence through the cutouts of the mask. For example, the surface can be irradiated through a film which has transparent and non-transparent regions. The covered regions of the surface represent the reference field (unchanged after the irradiation), while the uncovered regions represent the regions of reference sample (before irradiation) and the sample (after irradiation). The pattern produced, comprising regions of reference field and reference sample or sample, then corresponds to the pattern of the mask used for the covering and is described by an appropriate pattern function. The pattern can be, for example, a simple stripe or rectangular pattern.

In more general terms, therefore, the first and second two-dimensional pattern can be produced by a surface being covered with a mask which has regions that are permeable and impermeable to the environmental influence, and the environmental influence is allowed to act on the surface through this mask, and the regions of the surface covered by the impermeable regions of the mask forming the reference field and the regions of the surface subjected to the environmental influence forming the reference sample (before the action of the environmental influence) and sample (after the action of the environmental influence).

In a fifth step (v), for the first pattern, at a freely selectable time $t_0$ and, for the second pattern, at the time t, by means of a detector, the transmission, reflection or scattering of analytical radiation by the first pattern and the second pattern, respectively, is detected as a function of the local coordinates (x, y) of the first and second pattern, respectively, and of the wavelength $\lambda$ of the analytical radiation and thus a first pattern response function $M_0(x, y, \lambda, t_0)$, which contains physically separated regions of a reference response function $R_0(x, y, \lambda, t_0)$ and of a first reference field response function $RF_0(x, y, \lambda, t_0)$, is determined for the first pattern, a second pattern response function $M_t(x, y, \lambda, t)$, which contains physically separated regions of a sample response function $P_t(x, y, \lambda, t)$ and of a second reference field response function $RF_t(x, y, \lambda, t)$, is determined for the second pattern, the functions $M_0$ and $M_t$ in each case reproducing the intensity of the transmitted, reflected or scattered analytical radiation as a function of the local coordinates (x, y) of the first and second pattern, respectively, and of the wavelength $\lambda$ at the different times of the detection $t_0$ and t, To analyze the first and second pattern, respectively, the transmission, reflection or scattering of analytical radiation by the first and second pattern, respectively, is detected as a function of the location coordinates (x, y). The analytical radiation can have a discrete wavelength, for example the wavelength of the CO band at 5.8 µm (corresponding to 1720 $cm^{-1}$) or else cover a wavelength range, for example the entire visible spectral range from 400 to 800 nm. The transmission, reflection or scattering of the analytical radiation by the sample generally depends on the wavelength of the analytical radiation. Response functions are thus obtained which reproduce the intensity of the transmitted, reflected or scattered analytical light as a function of the location coordinates (x, y) and the wavelength $\lambda$. The response functions can be determined for discrete wavelengths $\lambda$ or for one or more wavelength ranges $\Delta\lambda$ (for example for the red, green and blue region of visible light).

The wavelength of the analytical radiation or its spectral composition depend on the example examined and on the question posed. The analytical light will often be in the UV-VIS and/or NIR range of the spectrum. For example, if the light fastness of colorants is to be examined, that is to say the change in the coloration in a treated sample that can be perceived by the human eye, then the analytical light will substantially have the spectral composition of daylight or be daylight. If, for example, the light-induced ageing of plastics is to be examined by determining the CO index of the plastics, then the analytical light will be NIR light with a wavelength around 5.8 μm. If the stability of UV absorbers is to be examined, then the analytical radiation will comprise UVA and/or UVB light.

The measuring setup used also depends on the sample examined and the question posed. For example, if the gloss behavior of a substrate surface, for example of a paint surface, is to be analyzed, then the use of telecentric measuring optics, which largely eliminates the influences of scattering from deeper layers of the sample, is suitable for this purpose. On the other hand, if the light fastness of colorants is to be examined, the use of a confocal color measuring system, which largely suppresses the disruptive influences of the gloss, is suitable for this purpose.

In one embodiment of the method according to the invention, the reflection of the analytical light by a substrate surface is determined. In this case, telecentric measuring optics are preferably used. In a further embodiment of the method according to the invention, the scattering of the analytical light by a substrate surface is detected. In this case, a confocal color measuring system is preferably used.

The reflection or scattering of the analytical radiation by the substrate surface as a function of the location coordinates (x, y) and of the wavelength λ can also be detected with a color scanner or a digital camera.

The detection of radioactive or acoustic radiation (ultrasound) can be carried out with imaging methods known from medical diagnostics. Thermal infrared radiation can be detected with a thermal image camera.

In order to make the change in the sample induced by the environmental influence better detectable, the sample can be subjected to a post-treatment. A change in the hydrophilic or hydrophobic properties of the sample can be made better detectable, for example, by the sample being dampened with water vapor.

By using the detected intensity values, the corresponding response functions are generally determined with a digital image evaluation system.

In a sixth step (vi), a correction to a sample response function $P_t$ is made in such a way that, by means of the first and the second reference field response function $RF_0$ and $RF_t$, the detector-induced location-dependent, time-dependent and wavelength-dependent fluctuations are eliminated from the sample response function $P_t$, a corrected sample response function $P_{t,corr}$ being obtained.

The reference field response functions $RF_t(x, y, \lambda, t)$ and $RF_0(x, y, \lambda, t_0)$ of the reference field at the time t (or, more generally, $t_i$, if a series of measurements is carried out at a plurality of times $t_i$) and $t_0$ respectively, are measured simultaneously with the sample response function $P_t(x, y, \lambda, t)$ and the reference response function $R_0(x, y, \lambda, t_0)$ respectively. The reference field response function $RF_t(x, y, \lambda, t)$ or $RF_0(x, y, \lambda, t_0)$ is then continued into the location region of the response function $P_t(x, y, \lambda, t)$ or $R_0(x, y, \lambda, t_0)$. In this way, location-dependent fluctuations of the detector are taken into account. Therefore, $RF_t$ and $RF_0$, respectively, are also available in the region of the coordinates x, y of the response function P. The correction of P with respect to the fluctuations over time of the detector is then carried out in accordance with the computational rule $$P_{t,corr}(x,y,\lambda,t)=RF_0(x,y,\lambda,t_0)/RF_t(x,y,\lambda,t) \times P_t(x,y,\lambda,t)$$

or, more generally, $$P_{ti,corr}(x,y,\lambda,t_i)=RF_0(x,y,\lambda,t_0)/RF_{ti}(x,y,\lambda,t_i) \times P_{ti}(x,y,\lambda,t).$$

The reference sample is preferably the untreated sample, of which the response function is determined at the time t=0. The abovedescribed correction for the response functions of the treated sample, which are determined at the time $t_i$, is then carried out.

Of course, the steps (i)-(vi) can also be carried out in any desired practical order. For example, the steps (vi) and (v) or (iv)-(vi) can be carried out first for the reference sample and then for the sample, or vice versa.

By using the corrected sample response function $P_{t,corr}$ and, if appropriate, the reference response function $R_0$, the change in the physically measurable property is determined. A number of possibilities are available for this purpose.

Variant A:

In step (vii), in each case an average of values of the corrected sample response function $P_{t,corr}$ and the reference response function $R_0$ is formed and these averages are compared with one another. The difference between the averages is a measure of the change in the physically measurable property.

Variant B:

In step (vii), a corrected pattern response function $M_{t,corr}$ is formed from the corrected sample response function $P_{t,corr}$ and the first reference field response function $RF_0$, and this corrected pattern response function $M_{t,corr}$ is correlated with the known location-dependent and wavelength-dependent pattern function M(x, y, λ), this correlation, which has a specific numerical value, being a measure of the change of the physically measurable property.

In a preferred embodiment of this variant B, in step (vii), a zero value pattern response function $N_0(x, y, \lambda, t_0)$ is additionally determined from the reference response function $R_0$ and the first reference field response function $RF_0$ and this is correlated with the known location-dependent and wavelength-dependent pattern function M(x, y, λ), this correlation representing the zero value of the correlation and the correlation obtained from the corrected pattern response function $M_{t,corr}$ being corrected by this zero value.

The zero value function is therefore determined on a pattern from reference sample and reference field. The zero value pattern response function and, respectively, the correlation obtained from this, reproduce the differences between the reference sample and the reference field. In addition, the zero value pattern response function and, respectively, the correlation reproduce the artefacts produced by the type of arrangement of regions of the reference field and the (reference) sample which, for example, can consist in a shadow when the (reference) sample is placed behind the reference field, and are independent of the differences between reference sample and sample and, respectively, the change in properties induced in the sample.

Strictly speaking, the reference field and the reference sample do not have to have exactly the same composition, that is to say for example consist of the same material, since such differences in the composition are registered by determining the zero value pattern response function and the correlation resulting from this and are taken into account by a corresponding correction value (zero value of the correlation). In order to keep this correction value as small as possible, however, it is preferred for the reference sample and reference field to have a substantially identical composition, at least at their surface.

Variant C:

In step (vii), regions of the corrected sample response function $P_{t,corr}$ and regions of the reference response function $R_0$ are mixed to form a virtual pattern, which is described by a location-dependent and wavelength-dependent virtual pattern function $M_v(x, y, \lambda)$, a virtual pattern response function $V_t(x, y, \lambda, t)$ being obtained by the mixing which, corresponding to the virtual pattern function $M_v$, contains regions of the corrected sample response function $P_{t,corr}$ and regions of the reference response function $R_0$ and, by means of correlation analysis, the correlation of the known location-dependent and wavelength-dependent virtual pattern function $M_v(x, y, \lambda)$ with the virtual pattern response function $V_t(x, y, \lambda, t)$ is determined, this correlation being a measure of the change in the physically measurable property.

In order to produce the virtual response function, regions of the corrected sample response function and regions of the reference response function are mixed to form a virtual pattern, which contains regions of both functions $P_t$ and $R_0$. The pattern is described by a freely selected location-dependent and wavelength-dependent virtual pattern function $M_v(x, y, \lambda)$. This virtual pattern function reproduces the geometric distribution of the regions of the sample response function and of the reference response function within the virtual pattern. This can vary with the wavelength $\lambda$ but does not have to.

For instance, the virtual pattern can be a bar code pattern, which is assembled from rectangular, elongated regions of the response function and of the reference response function. The virtual pattern can be, for example, a checkerboard pattern, which is assembled from square regions of the response function and of the reference response function. The virtual pattern can also be completely irregular. It is critical that the virtual pattern has both regions of the sample response function $P_{t,corr}$ and regions of the reference response function $R_0$, this pattern being described by a known, freely selected pattern function.

The virtual pattern, described by the virtual pattern function $M_v$, has to be distinguished from the (real) first and, respectively, second pattern of step (iv) and can be completely different from the latter. The latter is a real pattern comprising reference field and sample or reference sample, which is produced in order to carry out the abovedescribed reference field correction in order to eliminate temporal and local detector fluctuations. While the real pattern of step (iv) can be a relatively simple pattern, for example a pattern produced by a stencil having rectangular cutouts, and follows rather practical points of view (ability to manufacture an appropriate stencil), the virtual pattern can be completely arbitrary. In general, the virtual pattern will be produced by a data-processing system.

In the above described variants B and C, in each case a correlation analysis is carried out. During the correlation analysis, the pattern response function, which contains the information from the detection of the physically measurable properties, is correlated with the corresponding pattern function. In this case, the corrected pattern response function $M_{t,corr}$ based on the real pattern of step (iv) can be correlated with the corresponding pattern function M (variant B) or the virtual pattern response function $V_t$ can be correlated with the corresponding virtual pattern function $M_v$ (variant C).

The correlation analysis is a mathematical method known per se for the detection of characteristic patterns. Methods of correlation analysis have been described extensively in the literature. The extent to which the response function of the pattern correlates with a comparative function is examined. This method is to be sketched roughly below for the virtual pattern of variant C. It applies correspondingly to the real pattern of variant B. The precise configuration of the mathematical correlation analysis does not belong to the core of the invention.

For this purpose, a generalized correlation function is calculated:

$$K(\alpha, \beta, x_0, y_0, \lambda, t) = \int_{-\infty}^{\infty}\int_{-\infty}^{\infty} M(\alpha x + x_0, \beta y + y_0, \lambda) \cdot V(x, y, \lambda, t) dx dy$$

$\alpha$, $\beta$ are freely selectable scaling parameters, $x_0$, $y_0$ freely selectable position parameters. The above equation is to be understood to mean that the integration is carried out over two coordinates, but possibly over only one coordinate. The values for M and V for variables which exceed the measuring range are set equal to 0.

The correlation function provides information about the extent to which the pattern response function $V_t(x, y, \lambda t)$ is correlated with a pattern function (comparative function) $M(\alpha x+x_0, \beta y+y_0, \lambda)$ and how greatly this correlation changes when its variables are changed, that is to say how significant the correlation is.

The selection of the pattern function $M(\alpha x+x_0, \beta y+y_0, \lambda)$ depends on the question to be examined. The comparative function describes in general terms the change in the property, as is to be expected or is sought, of the sample or of the substrate surface as a result of the environmental influence, as is expected to be reflected in the regions of the real and virtual pattern respectively, which are formed from regions of the response function of the (treated) sample. Those skilled in the art will select a suitable comparative function on the basis of the question to be examined.

The pattern function M does not have to have any explicit wavelength dependence. However, if a color change is to be examined, for example, then the comparative function will have a wavelength dependence which, if appropriate, will be selected while taking account of human perception.

The correlation function merely images the desired change in the sample, that is to say that brought about by the environmental influence, and effectively suppresses interfering influences such as statistical noise, sample inhomogeneities and influences of external light. This results in a very high sensitivity.

One preferred variant of the general correlation analysis is Fourier analysis.

In one embodiment of the method according to the invention, the virtual pattern is a periodic pattern and, accordingly, the associated pattern function is a periodic pattern function with a local frequency $\alpha$. A periodic pattern is, for example, a bar code pattern.

As an example, in the following text a correlation analysis method for determining the correlation between the pattern function $M_v(x, y, \lambda)$ and the virtual response function $V_t(x, y, \lambda, t)$ will be described. Correlation analysis methods are known per se and have been described extensively in the literature. The invention therefore does not consist in providing such mathematical methods either. The explanations apply in a corresponding way to the real pattern (variant B).

If the pattern function has a periodic structure, the result is particularly clear relationships. For instance, if the pattern function $$M_v(x,y,\lambda) = \tfrac{1}{2}(1+\cos(\alpha_0 x))$$

is chosen and if it is then wished to determine the light fastness of a sample, it is true that $$K(\alpha, \beta, x_0, y_0, \lambda, t) = \int_{-\infty}^{\infty} \frac{1}{2} \cdot (1 + \cos(\alpha x)) \cdot V(x, y, \lambda, t) dx$$

Therefore, the correlation function is the real Fourier transformation of the response function, apart from a constant. α can thus be understood as a local frequency. Furthermore, only at the inherent frequency $\alpha_0$ does $K(\alpha, \beta, x_0, y_0, \lambda)$ exhibit a term which is brought about by the irradiation. At all the other local frequencies $\alpha \neq \alpha_0$ the correlation function vanishes. Thus, an infinitely high local frequency resolving power $\alpha_0/\Delta\alpha$ is obtained.

In practice, however, it is necessary to take account of the fact that, because of the finite sample size $x_{max}$, the integration cannot be carried out from minus infinity to plus infinity.

Furthermore, measurements are not made continuously; instead the response function is digitalized with a limited number of reference points. The density of the reference points results in an upper limit for the local frequency which can still be measured. By contrast, the finite sample size results in the finite local frequency resolving power $\alpha_0/\Delta\alpha$ which is given by $\alpha_0/\Delta\alpha = \alpha_0 \cdot x_{max}$.

This means that interference caused by statistical processes (signal noise) is suppressed less effectively than in the case of an infinitely high local frequency resolving power. In practice, however, it has been shown that, despite these restrictions, the method according to the invention has a sensitivity higher by more than one hundred times as compared with visual inspection.

The correlation determined in this way is a quantitative measure, which is independent of any subjective assessment, of the change in the physically measurable property of the sample brought about by the environmental influence.

The pattern recognition by means of correlation analysis results in a very high sensitivity of the detection of the changes brought about in the sample or on the substrate surface by the environmental influence. This sensitivity is very much higher than in any method which is based on the visual assessment of samples (for example by using comparative samples).

In one embodiment of the method according to the invention, the intensity values of the scattered or reflected light are summed over a wavelength range $\Delta\lambda$ and, for a plurality of different wavelength ranges $\Delta\lambda_1, \Delta\lambda_2, \Delta\lambda_3, \ldots$ a plurality of different sample response functions $P^1(x, y, \Delta\lambda_1)$, $P^2(x, y, \Delta\lambda_2)$, $P^3(x, y, \Delta\lambda_3)$, ... and a plurality of different reference response functions $R^1(x, y, \Delta\lambda_1)$, $R^2(x, y, \Delta\lambda_2)$, $R^3(x, y, \Delta\lambda_3)$ are determined and subjected to the abovedescribed reference field correction and correlation analysis (variants B and C). It is not possible to determine, for example, the extent to which the environmental influence acts on a specific property of the sample or substrate surface, which is reflected in the change in the absorption properties of the sample or of the substrate surface at a specific wavelength or in a specific wavelength range, while it leaves untouched other properties which would be reflected in the absorption properties of the sample or substrate surface at a different wavelength or in a different wavelength range.

In one embodiment of the method according to the invention, in each case response function and reference response function for red, green and blue light are determined by means of RGB analysis. This is done by the intensity values of the light reflected or scattered by the substrate surface being summed for the red, green and blue wavelength range, that is to say for the wavelength range of, for example, 600-700 nm (red), 500-600 nm (green) and 400-500 nm (blue), and a corresponding specific response function and specific reference response function being determined for each of these wavelength ranges. For instance, if the light fastness of colorants is to be examined, it is possible in this way to determine how the red, green and blue component of the light scattered by the colorant sample changes following irradiation (for example with sunlight) and how the color impression of the colorant changes as a result.

For example, a substrate surface can be irradiated through a grid film. The non-transparent regions of the grid film result in the reference field, while the transparent regions result in the (reference) sample. Following irradiation, the grid film is removed and the substrate surface is scanned in with a scanner. The R, G, B signals of the irradiated substrate surface are then subjected to a one-dimensional Fourier transformation in accordance with the method described below. Let the intensities measured by the scanner be designated $S_j(k, m)$. Here, the index designates the R, G, B colors (red, green and blue). By contrast, the variables k and m indicate the location at which the intensity was measured. The direction indicated by k or m will be designated the image line or image column in the following text.

With the aid of the mathematical operation:

$$P_j(k', m) = \sqrt{[\int_{all\ k} S_j(k, m) \cdot \sin(2 \cdot \pi \cdot k' \cdot k) \cdot dk]^2 + [\int_{all\ k} S_j(k, m) \cdot \cos(2 \cdot \pi \cdot k' \cdot k) \cdot dk]^2}$$

the power spectrum $P_j(k', m)$ is calculated for each image line.

The power spectra obtained in this way for each image line are averaged over all the image columns:

$$\overline{P_j(k')} = \frac{\sum_{all\ images\ lines} P_j(k', m)}{\text{No. of image lines}}$$

In the examples shown, in each case the averaged power spectrum $\overline{P_j(k')}$ is plotted against the local frequency k'. Photochemicallly induced changes in the color of the substrate surface can be detected clearly in the R, G, B channels as a result of the fact that, at the local frequency determined by the film grid, a considerably increased intensity of the averaged power spectrum is to be established. The height of this intensity in the individual channels R, G, B, is a measure of the photochemically produced color change.

For the purpose of more comprehensive examination of the sample, the result of the mathematical operation described is considered in more detail. In addition to the power spectrum, the sign of $$V_j(k', m) = \int_{all\ k} S_j(k, m) \cdot \cos(2 \cdot \pi \cdot k' \cdot k) \cdot dk$$

is now also taken into account. In order to suppress noise, in this case averaging over all the image lines measured $$V_f(k')) = \frac{\sum_{all\ images\ lines} V_j(k', m))}{No.\ of\ images\ lines}$$

is also carried out. $V_j(k')$ provides information as to whether the environmental influence has led to an increase ($V_j(k')>0$) or to a decrease ($V_j(k')<0$) in the signal measured by the scanner.

Substrate surfaces which can be examined with the present method are the surfaces of any desired materials, for example the surfaces of plastics, wood, paint and paper.

Changes of properties of the substrate materials themselves, for example of plastics, can be examined, or changes of properties of substances which have been introduced into the substrate materials or have been applied to the latter, for example of colorants, UV absorbers, stabilizers, cosmetic formulations.

One aspect of the present invention is the use of the method according to the invention for examining the thermally or light-induced ageing of plastics by means of locally resolved detection of the CO band at 5.8 μm. For this purpose, as described in DIN 53383, inter alia, the ratio of the extinction at 5.8 μm to a specific reference extinction which, for the plastic polyethylene, for example, lies at 4.95 μm (corresponding to 2020 $cm^{-1}$) is formed.

Likewise, the thermally or light-induced (photooxidative) ageing of any further desired substances can be examined. A further aspect of the invention is therefore, generally, the use of the method according to the invention for examining the light-induced or photooxidative ageing of substances. Substances to be examined are, for example, plastics colored with colorants or uncolored plastics, paints, metals, textiles, papers, wooden articles or building materials.

The detection of the light-induced ageing is carried out via suitable spectroscopic bands of the relevant substance. These can lie in the IR or UV-VIS range of the spectrum.

One aspect of the present invention is also the use of the method according to the invention for determining the light fastness of colorants. Colorants can be dyes or pigments. In this case, the procedure can be such that a substrate surface which contains the colorant is irradiated, preferably with sunlight or light from a sun simulator. Suitable sun simulators and light sources which have an emission spectrum corresponding to sunlight, are known to those skilled in the art and, for example, comprise a xenon lamp. In open-air trials, the sample can also be irradiated with sunlight directly or indirectly by means of a system of mirrors through a suitable weather-resistant metal mask. The irradiation intensity for UV light in the wavelength range up to 400 nm is, for example, 20 to 2000 $W/m^2$ and, for light in the visible spectral range from 400 to 800 nm, is 500 to 5000 $W/m^2$, in particular for UV light it is about 50 $W/m^2$ and therefore corresponds to the radiation intensity of natural sunlight. The irradiation period (action period Δt) can be from a few seconds to several years. For very light-fast or weathering resistant samples, it is generally one week to a few months. The method according to the invention for determining the light fastness of colorants is distinguished by the fact that a relatively short irradiation period with a natural radiation intensity is already sufficient to make the color change of the sample detectable quantitatively. Following irradiation, the irradiated substrate surface and the reference field are scanned in with a scanner or recorded with a digital camera. Furthermore, the surface of a non-irradiated reference sample and the reference field are scanned in or recorded with a digital camera. Then, by using image evaluation electronics, an RGB analysis is preferably carried out and the response functions for red, green and blue light and also the corresponding reference response functions for the non-irradiated reference sample are determined and subjected to the reference field correction. The corrected sample response functions for red, green and blue light and the corresponding reference response functions are assembled to form virtual patterns with a known pattern function, a virtual response function resulting for each of the colors red, green and blue (variant C). These are finally correlated with the known pattern function of the virtual pattern, a Fourier analysis preferably being carried out as the correlation analysis. The peak of the correlation function for red, green and blue light at the local frequency of the pattern corresponds quantitatively to the change in the red, green and blue color component in the light scattered by the substrate surface which can be attributed to the irradiation. In a corresponding way, a correlation analysis can be carried out on the real pattern comprising reference field and (reference) sample (variant B). This real pattern can be produced by means of irradiation or weathering through a mask, the covered regions representing the reference field, or by covering the non-irradiated and, respectively, irradiated sample with a (reference field) stencil, corresponding to one of the variants described above.

A further aspect of the invention is the use of the method according to the invention for determining the change in the gloss behavior of a substrate surface. Substrate surfaces to be examined are, for example, paint surfaces, preferably those of automobile paints. For example, it is possible to examine the extent to which the environmental influence leads to mechanical damage to the substrate surface, which is reflected in a change in the gloss behavior of the substrate surface. For instance, cracks or voids can be formed in a paint layer. In order to detect such changes, the reflection of analytical light is measured with the aid of telecentric illumination and detection optics. Using a telecentric measuring arrangement ensures that the sample is illuminated with parallel analytical light and only parallel light is detected. As a result, only changes in the gloss behavior of the sample are detected and possible changes in the color of the sample are suppressed.

A further aspect of the method according to the invention is the diagnosis of allergic skin irritations of the human or animal skin which are caused by environmental influences, for example by cosmetic formulations or generally by allergenic substances. By means of the method according to the invention, early detection of the allergic skin irritation is possible, long before the skin irritation is perceptible by the eye.

A further aspect of the method according to the invention is the examination of the effectiveness of agricultural chemicals used in agriculture, such as fertilizers, fungicides, herbicides and insecticides. The substrate surface here is a part of the surface of the earth which is cultivated with useful plants, the environmental influence is the introduction of the chemicals into the soil or the application of the chemicals to the useful plants. An aerial photograph of the treated field and an untreated field are taken, are digitally processed and, if appropriate following an RGB analysis, are assembled to form a virtual pattern. This is subjected to a correlation analysis.

Further aspects of the invention are the use of the method according to the invention for examining the weathering resistance of substances, the chemical resistance of substances or the abrasion resistance of coatings.

For instance, the method according to the invention can be used in conjunction with the methods described in the relevant standards for weathering with artificial daylight or for direct weathering. Relevant standards are, for example, ISO 4892 (1994) for plastics, ISO 11341 (1994) for paints and varnishes, ISO 1507 (1997) for coatings in instruments, ISO 3917 (1999) for road vehicle safety panels, ISO 11431 (2002) for civil engineering joint sealants, ISO 105-B02 (1994) for textile color fastness tests and ISO 105-B04 (1994) for textile color fastness in weathering, and also ASTM G7, ISO 877, ISO 2810, ASTM D4141C (Black Box) and ASTM G24 (exposure under glass) for direct weathering.

Thus, inter alia, the following weathering or exposure devices and boxes can advantageously readily be used:

- all the devices which can already be obtained commercially for artificial exposure or weathering (see examples);
- in the case of open-air weathering, for example, the "Black Boxes" (for example from the ATLAS company);
- exposure chambers for exposure under glass (for example from the ATLAS company);
- weathering apparatus with automatic tracking for the path of the sun, for example the IP/DP box from the ATLAS company in Arizona and Florida;
- weathering systems with accelerated rainfall and solar exposure by means of suitable mirror systems (for example EMMA/EMMAQUA from the ATLAS company).

The invention will be explained in more detail by means of the following examples.

EXAMPLES

Example 1

A 6 cm×10 cm paint sample from BASF AG with a 1:5 white reduction of P.R.63:1, before exposure, was placed downward on the object platen of an ARTIXSCAN scanner from the Miktrotec company and was scanned in with a resolution of 150 dpi with 48-bit depth of color.

A transparent film was then printed with a black, non-transparent bar having a width of 2 cm and a length of 10 cm in each case in the left-hand and in the right-hand third of the film with the aid of an HP 2000 C inkjet printer. The film was fixed to the paint sample in such a way that exactly two thirds of the paint sample were covered by the two outer black stripes.

The paint sample with film was exposed for a total of 300 minutes under outdoor conditions in an XLA Plus Suntester from the ATLAS company. At regular time intervals, the paint sample was removed from the exposure device, the film was removed and the paint sample was placed with the exposed side downward onto the object platen of the scanner and scanned in with the same device parameters as during the scanner operation before exposure.

The R, G, B signals from the irradiated paint sample were then corrected, by means of the reference field correction described above, with respect to the scan before the first exposure of the paint sample, the two outer thirds of the paint sample covered with black during the exposure forming the reference field, the inner unexposed stripe the reference sample and the inner exposed stripe the sample.

By using a personal computer, the corrected reflection values determined in this way from the central third of the paint sample (sample) were mixed, as described above, with the aid of the reflection values of the central third before the exposure (reference sample) to form a virtual response function with a local frequency of 3/mm. A one-dimensional Fourier transformation taking the phase into account supplied the changes in the reflectances for the channels R, G and B caused by the exposure operation.

This analysis was carried out after each exposure interval. The radiation-induced changes in the reflection values of the sample, cleaned of the fluctuations of the scanner, were determined for various irradiation times $t_i$ in this way and plotted against the time. The result is reproduced in FIG. 1. In this case, the irradiation time in minutes is plotted on the abscissa and the change in the reflectance in % is plotted on the ordinate.

Figure 1:
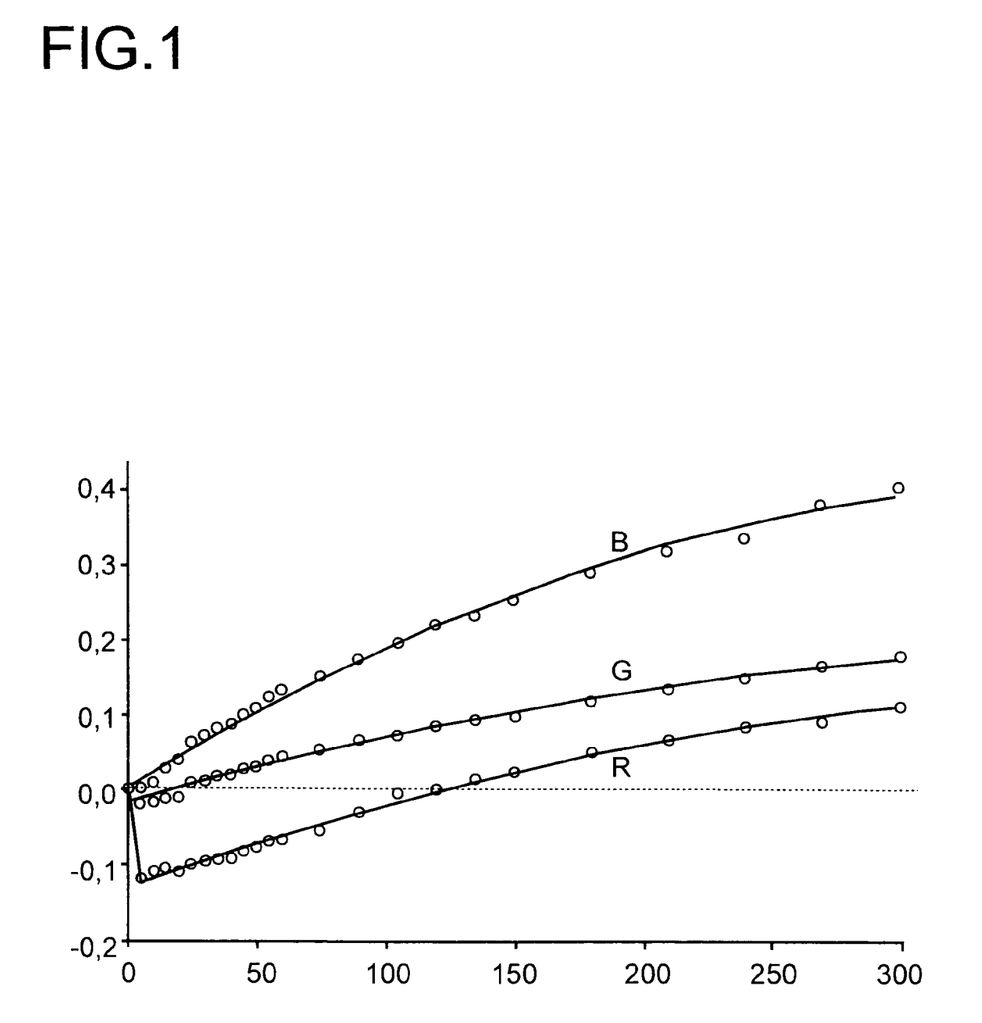
FIG. 1 shows the results of Example 1 according to an embodiment of the present disclosure.

In all three channels R, G and B, a monotonically rising increase in the reflectances with increasing irradiation time is observed. This corresponds to a lightening of the exposed sample. The sharp drop in the reflectance in the red channel after only a few minutes was reproduced in a number of experiments. The minimum irradiation time for a lightening effect that is clearly visible to the eye was around 600 minutes in this example. This demonstrates the very high sensitivity of the method. The individual measured points deviate only by about 0.01 to 0.03% from the curves matched to the measured points by regression analysis.

Example 2

The procedure was the same as that described in example 1, but the reference field used was a stencil comprising a metal sheet painted with the pigment P. R. 63:1 and having the dimensions 20×9 cm and a thickness of 2 mm, which had 4 regularly arranged rectangular cutouts having the dimensions 2.5×7 cm. Relatively small sheet metal samples having the same dimensions, which were painted in the same way with the pigment P.R. 63:1, were placed in this stencil with an accurate fit as a reference (sample).

The four sheet metal samples P were identical, were exposed together and, after each time interval, were inserted into the cutouts and scanned in together with the reference field stencil. For this purpose, the reference field R was mounted permanently on the scanner glass with the painted side downward. The evaluation of the scanner signals (R, G, B signals) was carried out as in example 1.

Figure 2:
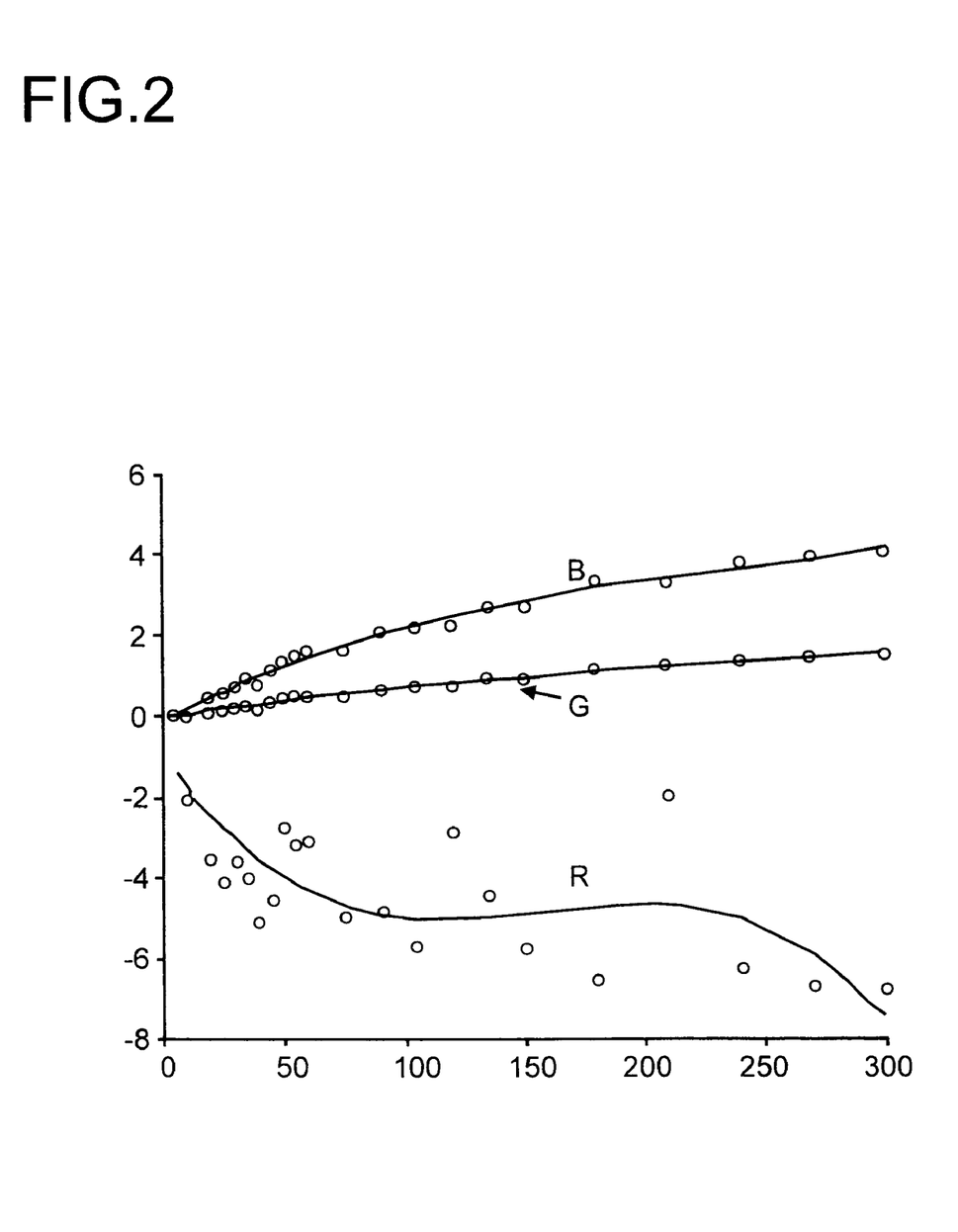
FIG. 2 shows the results of Example 2 according to an embodiment of the present disclosure.

The results are reproduced in FIG. 2. In this case, the irradiation time in minutes is plotted on the abscissa and the change in the reflectance in % is plotted on the ordinate.

Since the individual sheet metal samples were not exposed through a film, a somewhat more intense, light-induced lightening with increasing irradiation time is observed in the blue and green channels. In the red channel, however, a decrease in the reflectance (darkening) with increasing irradiation time is observed, the measured points being scattered considerably more than in example 1. The scatter of these measured points does not impair the sensitivity of the method, however, since the light-induced color changes in the paint samples, visually perceptible only after a much longer irradiation time (of considerably more than 300 min) can be attributed substantially to the changes in the reflectance in the region of the blue and green channels, which lie in the region of the absorption of the paint pigments.

Example 3

The procedure was the same as in example 2, and the same stencil as in example 2 was used as reference field. This was painted with a test paint from BASF having a white reduction of P.B. 15:3. Instead of the 4 small paint samples, however, a single large sheet metal sample having the dimensions of the reference field stencil was exposed under outdoor conditions. During each scanning operation, the sheet metal sample was placed with the painted side on the reference field stencil. The spacing of the sample surface from the scanner platen was 2 mm, corresponding to the thickness of the stencil. In order to eliminate the effects (artefacts) induced by the different spacing of reference field and sample from the scanner platen, the zero value correction described above was carried out. Otherwise, the evaluation of the measured signals corresponded to examples 1 and 2.

Figure 3:
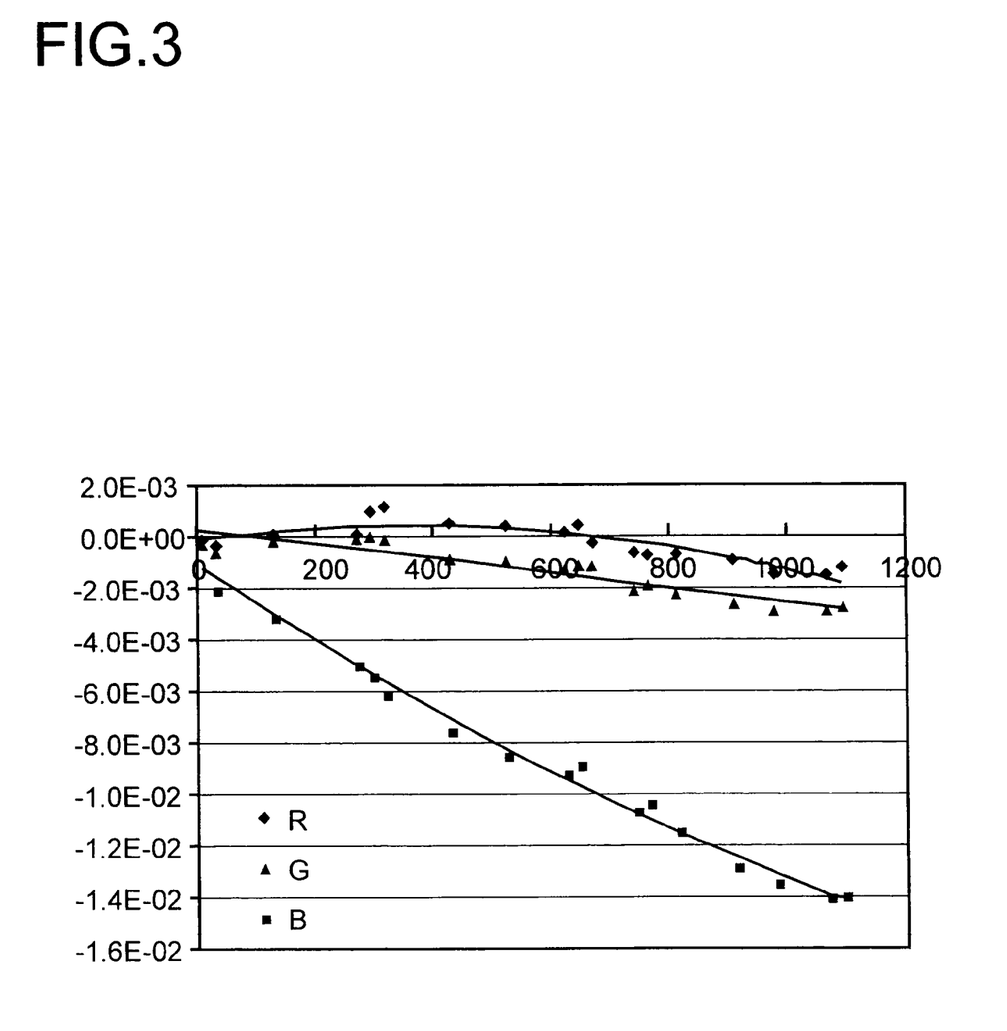
FIG. 3 shows the results of Example 3 according to an embodiment of the present disclosure.

The results are reproduced in FIG. 3. In this case, the irradiation time in hours is plotted on the abscissa and the relative change in the reflectance (1=100%) is plotted on the ordinate.

Darkening of the test paint with increasing exposure as a result of the decrease in the reflectance in the blue channel is substantially observed. The darkening can also be detected visually from about 1200 hours irradiation time. The high measurement accuracy of this method already permits the prediction of this visually perceptible effect by means of extrapolation after a much shorter irradiation time.

Example 4

The procedure is the same as in example 3, but, instead of the exposure, rapid weathering in a commercial weathering device (W.O.M CI 35 A from the ATLAS company) is carried out in accordance with the test method SAE 1960, CAM 180.

Figure 4:
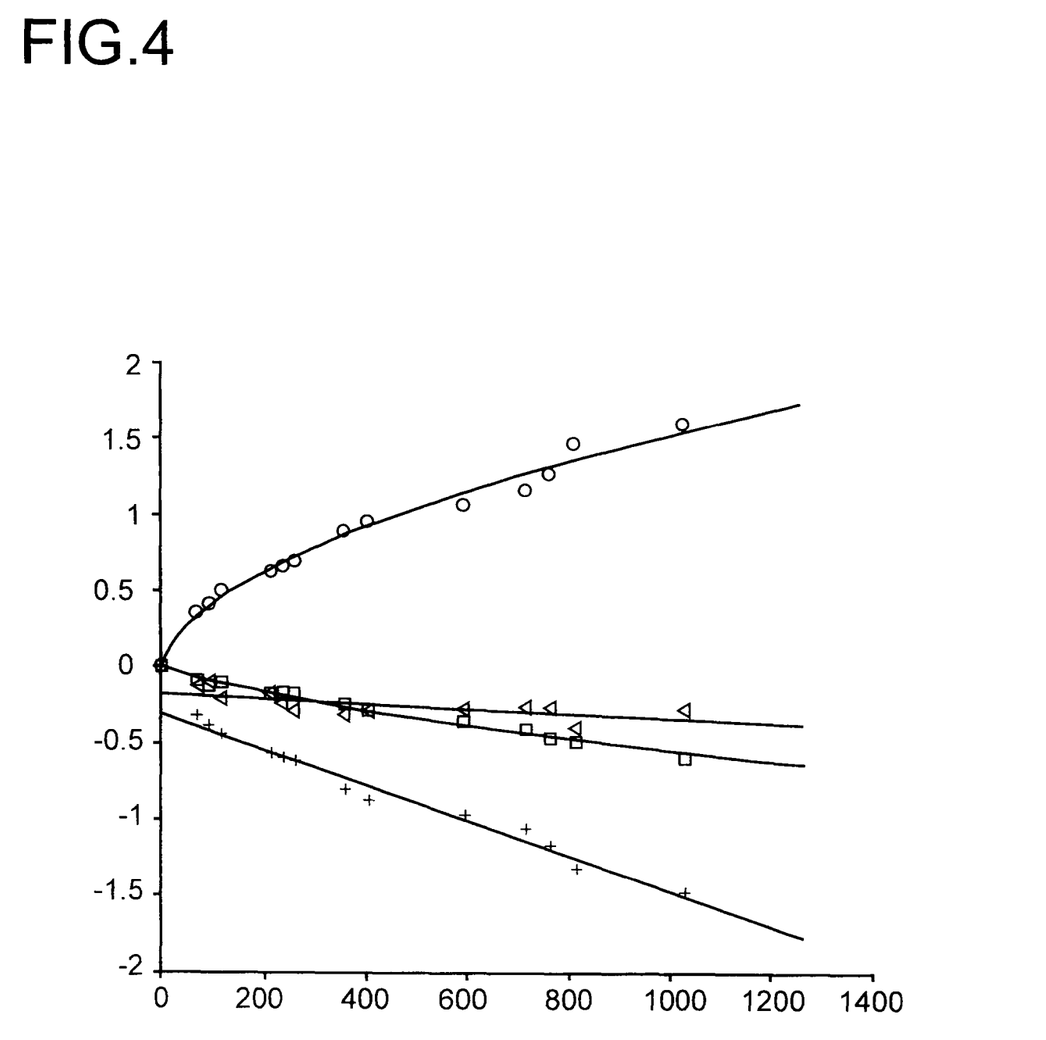
FIG. 4 shows the results of Example 4 according to an embodiment of the present disclosure.

Conversion of the weathering-induced reflectance changes into CIELAB color coordinates supplies the results illustrated in FIG. 4:

The weathering time in hours is plotted on the abscissa. The following are plotted on the ordinate:

++++: change in chroma ($\Delta C$)

□□□□: change in hue ($\Delta H$)

○○○○: color difference ($\Delta E76$)

ΔΔΔΔ: change in lightness ($\Delta L$)

Here, too, the high accuracy of the method according to the invention also permits the prediction of effects that are generally visually perceptible only after 1000 to 2000 weathering hours, by means of extrapolation of the values obtained at much shorter weathering times.

We claim:

1. A method for detection of differences between physically measurable properties of a sample and a reference sample, comprising:
   (i) providing a sample;
   (ii) providing a reference sample;
   (iii) providing a two-dimensional reference field;
   (iv) producing a first two-dimensional pattern from regions of the reference sample and from the reference field, and producing a second two-dimensional pattern from regions of the sample and of the reference field, the first and second patterns being described by a location-dependent and wavelength-dependent pattern function;
   (v) detecting, for the first pattern, at a freely selectable time, and for the second pattern, at a time by a detector, transmission, reflection or scattering of analytical radiation by the first pattern and the second pattern, respectively, as a function of local coordinates of the first and second patterns, respectively, and of the wavelength of the analytical radiation and thus a first pattern response function, which contains physically separated regions of a reference response function and of a first reference field response function, is determined for the first pattern,
   a second pattern response function, which contains physically separated regions of a sample response function and of a second reference field response function, is determined for the second pattern,
   the first and second pattern response functions in each case reproduce intensity of the transmitted, reflected or scattered analytical radiation as a function of the local coordinates of the first and second patterns, respectively, and of the wavelength at different times of the detection,
   (vi) making a correction to a sample response function by a data processing system such that, by the first and the second reference field response functions, detector-induced location-dependent, time-dependent and wavelength-dependent fluctuations are eliminated from the sample response function, and obtaining a corrected sample response function; and
   (vii) determining, by the data processing system, a change in the physically measurable property from the corrected sample response function and the reference response function.

2. The method as claimed in claim 1, wherein, in the determining (vii), in each case an average of values of the corrected sample response function and the reference response function is formed and these averages are compared with one another.

3. The method as claimed in claim 1, wherein, in the determining (vii), a corrected pattern response function is formed from the corrected sample response function and the first reference field response function, and this corrected pattern response function is correlated with the known location-dependent and wavelength-dependent pattern function, this correlation being a measure of the change of the physically measurable property.

4. The method as claimed in claim 3, wherein, in the determining (vii), a zero value pattern response function is additionally determined from the reference response function and the first reference field response function and is correlated with the known location-dependent and wavelength-dependent pattern function, this correlation representing the zero value of the correlation and the correlation obtained from the corrected pattern response function being corrected by this zero value.

5. The method as claimed in claim 1, wherein, in the determining (vii), regions of the corrected sample response function and regions of the reference response function are mixed to form a virtual pattern, which is described by a location-dependent and wavelength-dependent virtual pattern function, a virtual pattern response function being obtained by the mixing which, corresponding to the virtual pattern function, contains regions of the corrected sample response function and regions of the reference response function and, by correlation analysis, correlation of the known location-dependent and wavelength-dependent virtual pattern function with the virtual pattern response function is determined, this correlation being a measure of the change in the physically measurable property.

6. The method as claimed in claim 5, wherein the environmental influence is selected from action of mechanical forces, action of chemicals, action of gases, action of microorganisms, action of radioactive radiation, action of sound waves, or action of heat.

7. The method as claimed in claim 1, wherein the reference field surrounds or penetrates the sample or reference sample, respectively.

8. The method as claimed in claim 1, wherein the difference between the physically measurable properties of the sample and of the reference sample is brought about by the fact that the sample is subjected to an environmental influence and the reference sample is a corresponding sample that is not subjected to the environmental influence.

9. The method as claimed in claim 8, wherein the environmental influence is effected by weathering the sample.

10. The method as claimed in claim 1, wherein the first two-dimensional pattern is produced from regions of the reference sample and of the reference field, and the second two-dimensional pattern is produced from regions of the sample and of the reference field by the reference field being configured as a stencil having at least one cutout, and the reference sample or the sample are arranged behind the at least one cutout or in the at least one cutout of the stencil.

11. The method as claimed in claim 1, wherein the first and second two-dimensional patterns are produced by a surface being covered with a mask that has regions that are permeable and impermeable to an environmental influence, and the environmental influence is allowed to act on the surface through this mask, the regions of the surface covered by the impermeable regions of the mask forming the reference field, and the regions of the surface subjected to the environmental influence forming the reference sample, before action of the environmental influence and, respectively, the sample after the action of the environmental influence.

12. The method as claimed in claim 1, wherein, in the determining (iv), the transmission, reflection or scattering of analytical light in the UV-VIS and/or NIR range is determined.

13. The method as claimed in claim 12, wherein the transmission, reflection or scattering of analytical radiation is determined for a plurality of wavelength ranges and wavelength-specific response functions are determined for each wavelength range.

14. The method as claimed in claim 13, wherein the reflection or scattering of the analytical light as a function of the local coordinates is detected with a color scanner.

15. The method as claimed in claim 13, wherein the reflection or scattering of the analytical light as a function of the local coordinates is detected with a digital camera.

16. The method as claimed in claim 1, wherein the first and second patterns or the virtual pattern are periodic patterns with a local frequency.

17. The method as claimed in claim 1, wherein abrasion resistance of coatings on a substrate is examined.

18. The method as claimed in claim 1, wherein the differences between the sample and reference sample are detected for purpose of quality control.

* * * * *